United States Patent
Forster

(10) Patent No.: US 9,656,051 B2
(45) Date of Patent: **\*May 23, 2017**

(54) DEVICES WITH SELECTIVELY PERMEABLE BARRIERS

(71) Applicant: Avery Dennison Corporation, Pasadena, CA (US)

(72) Inventor: Ian J. Forster, Essex (GB)

(73) Assignee: AVERY DENNISON RETAIL INFORMATION SERVICES, LLC, Westborough, MA (US)

( \* ) Notice: Subject to any disclaimer, the term of this patent is extended or adjusted under 35 U.S.C. 154(b) by 230 days.

This patent is subject to a terminal disclaimer.

(21) Appl. No.: 13/690,189

(22) Filed: Nov. 30, 2012

(65) Prior Publication Data

US 2013/0144133 A1 Jun. 6, 2013

Related U.S. Application Data

(60) Provisional application No. 61/565,565, filed on Dec. 1, 2011.

(51) Int. Cl.
*A61B 5/1455* (2006.01)
*A61M 35/00* (2006.01)
*A61B 5/145* (2006.01)

(52) U.S. Cl.
CPC ............. *A61M 35/00* (2013.01); *A61B 5/145* (2013.01)

(58) Field of Classification Search
USPC .................................................. 600/310–344
See application file for complete search history.

(56) References Cited

U.S. PATENT DOCUMENTS

| 4,920,989 A | 5/1990 | Rose et al. |
|---|---|---|
| 4,983,395 A | 1/1991 | Chang et al. |
| 5,880,752 A * | 3/1999 | Weber et al. .................... 347/15 |
| 6,349,671 B1 * | 2/2002 | Lewis et al. ............... 119/51.02 |
| 2003/0099694 A1 | 5/2003 | Cevc et al. |

\* cited by examiner

*Primary Examiner* — Tse Chen
*Assistant Examiner* — Marjan Fardanesh
(74) *Attorney, Agent, or Firm* — Avery Dennison Retail Information Services, LLC

(57) ABSTRACT

Devices having selectively permeable barriers are provided with a substrate, a first layer overlaying at least a portion of the substrate, and a second layer overlaying at least a portion of the first layer. The first layer has at least one first pore and the second layer has at least one second pore. At least a portion of the first and/or second layers are movable with respect to each other between an open condition and a closed condition in response to a change in an environmental factor. In the open condition, the first and second pores are substantially aligned to allow fluid communication between the substrate and the outside environment. In the closed condition, the first and second pores are substantially misaligned to prevent fluid communication between the substrate and the outside environment.

12 Claims, 3 Drawing Sheets

DEVICES WITH SELECTIVELY PERMEABLE BARRIERS

CROSS-REFERENCE TO RELATED APPLICATION

The present application claims the benefit of U.S. Provisional Patent Application No. 61/565,565 filed Dec. 1, 2011, which is incorporated herein by reference in its entirety.

FIELD OF THE DISCLOSURE

The present subject matter relates to devices with selectively permeable barriers and methods employing the same. More particularly, the present subject matter relates to changing the permeability of a barrier in response to a change in an environmental factor.

DESCRIPTION OF RELATED ART

Numerous devices and methods are known for administering fluid. In one common application, a drug or treatment substance or fluid is applied to human skin (e.g., a wounded area of the skin) using a transdermal patch. For example, nicotine patches, such as the one described in U.S. Pat. No. 4,920,989 to Rose et al. (which is hereby incorporated herein by reference), are popularly used to assist people in quitting smoking. The patch is applied to the skin and, over time, nicotine is administered into the body through the skin. Other devices and methods for transdermal fluid administration are described in U.S. Pat. No. 4,983,395 to Chang et al. and U.S. Patent Application Publication No. 2003/0099694 to Ceve, et al., which are hereby incorporated herein by reference. Fluid administration patches and devices may also be used in other fields besides treatment of a human subject.

Such known fluid administration devices and methods may be disadvantageous in that they have a general lack of broad utility. While they are suitable for the applications for which they are designed, the number of applications is relatively small. Accordingly, it would be advantageous to provide more versatile fluid administration and fluid access devices and methods.

SUMMARY OF THE INVENTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, a device for allowing selective communication between a substrate and an outside environment includes a substrate, a first layer overlaying at least a portion of the substrate, and a second layer overlaying at least a portion of the first layer. The first layer has at least one first pore and the second layer has at least one second pore. At least a portion of the first and/or second layers are movable with respect to each other between an open condition and a closed condition in response to a change in an environmental factor. In the open condition, the first and second pores are substantially aligned to allow a direct pathway facilitating, for example, fluid communication between the substrate and the outside environment. In the closed condition, the first and second pores are substantially misaligned to block the pathway so as to interfere with communication therethrough, such as in order to prevent fluid communication between the substrate and the outside environment.

In another aspect, a method is provided for exposing a sensor to an environment. The sensor is separated from an environment by a first layer having a first pore and a second layer having a second pore. The first and second pores are positioned substantially out of alignment with each other and an environmental factor is changed. Changing the environmental factor moves the first and second pores into substantial alignment with each other and exposes the sensor to the environment via the first and second pores.

In yet another aspect, a method is provided for dispensing a dispensable material to an environment. The dispensable material is separated from an environment by a first layer having a first pore and a second layer having a second pore. The first and second pores are positioned substantially out of alignment with each other and an environmental factor is changed. Changing the environmental factor moves the first and second pores into substantial alignment with each other and allows the dispensable material to flow through the first and second pores and into the environment.

DETAILED DESCRIPTION OF THE ILLUSTRATED EMBODIMENTS

The embodiments disclosed herein are exemplary only, and the subject matter described herein may be embodied in various forms. Therefore, specific details disclosed herein are not to be interpreted as limiting the subject matter as defined in the accompanying claims.

Figure 1:
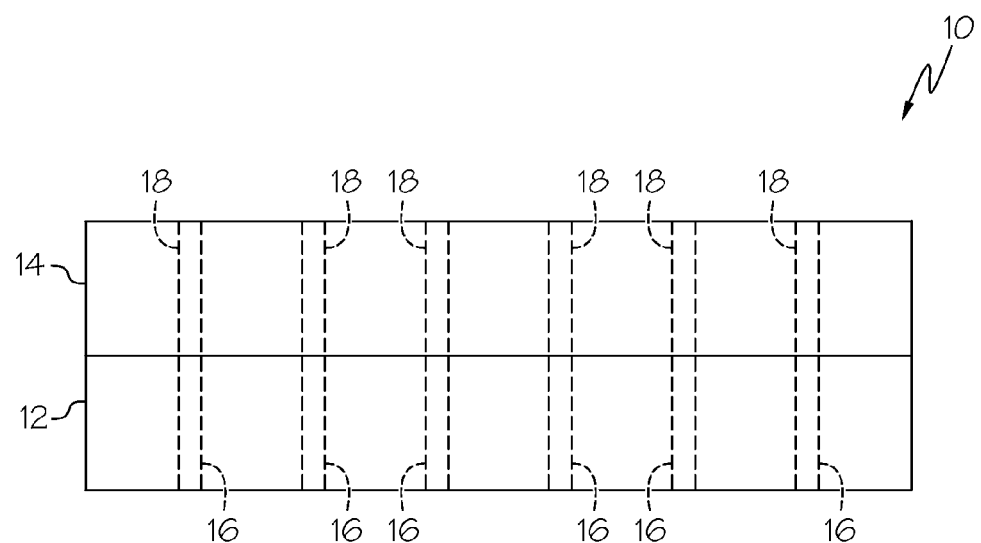
FIG. 1 is a schematic diagram of first and second layers of a selectively permeable barrier in an open condition.
Figure 2:
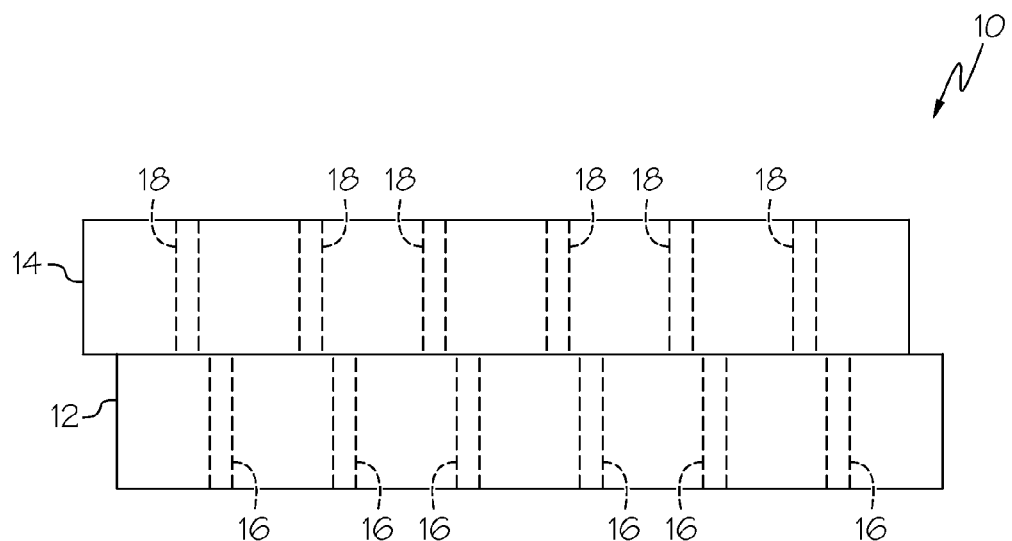
FIG. 2 is a schematic diagram of the barrier of FIG. 1 in a closed condition.

FIGS. 1 and 2 show a selectively permeable barrier 10, which includes a first or lower layer 12 and a second or upper layer 14. The second layer 14 overlays at least a portion of the first layer 12, and in at least some embodiments preferably overlays the entire first layer 12. The first and second layers 12 and 14, respectively, may be made from a variety of materials including, but not limited to, plastic, aluminum, and a "sandwich" or combination of plastic and aluminum. Most advantageously, the first and second layers 12 and 14 are configured to react differently to a change in an environmental factor, as will be described in greater detail herein.

The first layer 12 includes at least one first pore, aperture, or opening 16 and the second layer 14 includes at least one second pore, aperture, or opening 18. The pores 16 and 18 may be formed by any method but, in an illustrative embodiment, are formed using a laser-cutting operation. Other means for forming the pores 16 and 18 (e.g., photo-etching) may be employed without departing from the scope of the present disclosure. As shown in FIG. 1, each first pore 16 is substantially aligned with an associated second pore 18 when the barrier 10 is in an open condition. Thus, it may be advantageous for the first and second pores 16 and 18 to be formed simultaneously while the first and second layers 12 and 14 are face-to-face with each other to ensure their proper alignment.

With the first and second pores 16 and 18 in substantial alignment, as in FIG. 1, fluid may pass through the pores from one side of the barrier 10 to the other. Depending on the device into which the barrier 10 is incorporated and the nature and configuration of the pores, the fluid or other material, such as gas, solid (in the form of powder) mixtures, colloids and the like, passing through the barrier 10 may vary. For example, in one embodiment, a gaseous fluid (e.g., air), powders, mixtures, is configured to pass from the outside environment, through the barrier 10, and into an interior portion of a device overlaid by the barrier 10. In another embodiment, a liquid fluid, gas, mixture of colloids, powders, is configured to pass from the outside environment, through the barrier 10, and into an interior portion of a device overlaid by the barrier 10. In yet another embodiment, a dispensable fluid or material is initially stored in an interior portion of a device overlaid by the barrier 10. When the pores 16 and 18 are in substantial alignment, the dispensable fluid or material is released through the barrier 10 and into the outside environment. Specific examples of devices showing different fluid-transfer applications will be described in greater detail herein.

While FIG. 1 shows the first and second pores 16 and 18 in substantial alignment, they are substantially misaligned when the barrier 10 is in the closed condition of FIG. 2. Preferably, the associated first and second pores 16 and 18 are completely misaligned to prevent fluid flow therethrough. For example, in the illustrated embodiment, the individual pores 16 and 18 remain open (i.e., have the same configuration as in the open condition of FIG. 1) rather than individually closing or shutting. Instead, the associated pores 16 and 18 as shown in FIG. 2 are completely out of alignment to prevent fluid flow through the barrier 10. While it may be preferred for the first and second pores 16 and 18 to be completely out of alignment in the closed condition, it is within the scope of the present disclosure for the pores 16 and 18 to be only partially misaligned in the closed condition. When the pores 16 and 18 are only partially or substantially misaligned, it creates a torturous fluid path through the barrier 10 to discourage or, in some cases, prevent fluid transfer therethrough. The extent of flow therethrough can be dependent at least in part, for example, on the viscosity of the fluid.

Figure 3:
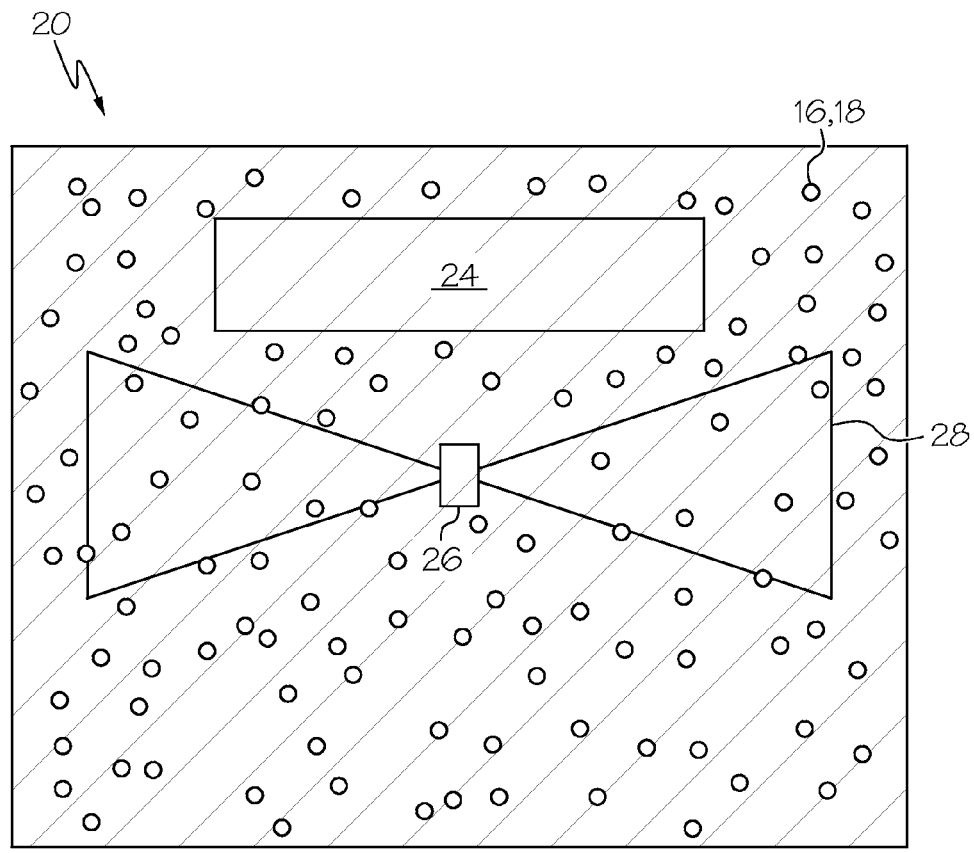
FIG. 3 is a top plan view of a sensor device incorporating a selectively permeable barrier.
Figure 4:
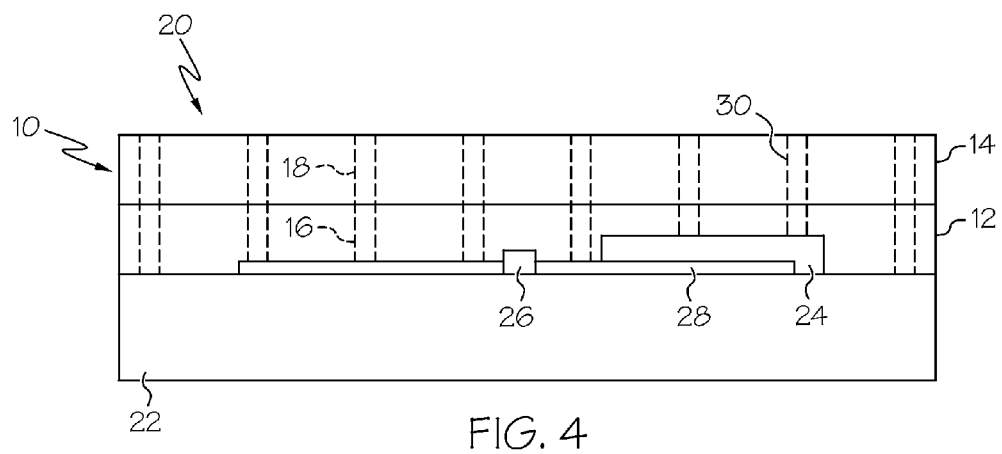
FIG. 4 is a side elevational view of the sensor device of FIG. 3.
Figure 5:
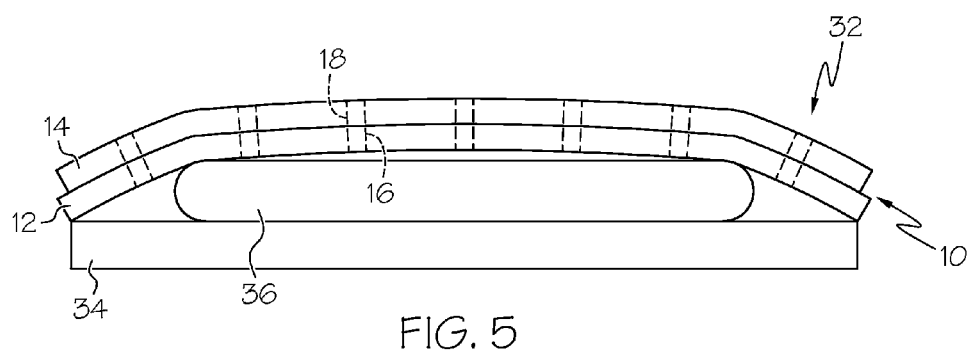
FIG. 5 is a side elevational view of a dispenser device incorporating a selectively permeable barrier.

The layers 12 and 14 of the barrier 10 are movable between the open (FIG. 1) and closed (FIG. 2) conditions in response to a change in an environmental factor. The environmental factor may vary depending on the nature of the device into which the barrier 10 is incorporated and the nature of the layers 12 and 14 themselves. For example, at least a portion of the first and/or second layers 12 and 14 may be movable with respect to each other in response to a temperature change. The relative change in position of the first and second pores 16 and 18 may be due to the first and second layers 12 and 14 having different thermal expansion coefficients, such that the first and second pores 16 and 18 are substantially aligned at one temperature (as in FIG. 1) and substantially misaligned at another temperature (as in FIG. 2). In another embodiment, the first and second layers 12 and 14 may have the same or similar thermal expansion coefficients, but different orientation access, such that the first and second pores 16 and 18 are substantially aligned at one temperature (as in FIG. 1) and substantially misaligned at another temperature (as in FIG. 2). FIGS. 3-5 illustrate devices incorporating barriers 10 which change fluid transmissibility depending on temperature.

FIGS. 3 and 4 illustrate a sensor device 20 employing the barrier 10 of FIGS. 1 and 2. In the context of FIGS. 3 and 4, the barrier 10 is an over-laminate that overlays at least a portion of a substrate 22, as best shown in FIG. 4. In particular, the barrier 10 is oriented with the first layer 12 overlaying at least a portion of the substrate 22 and the second layer 14 overlaying at least a portion of the first layer 12. Most preferably, the perimeter of the barrier 10 forms a fluid-tight seal with the substrate 22 to ensure that fluid can only enter the interior of the sensor device 20 through the pores when the barrier 10 is in the open condition.

The substrate 22 includes sensor material 24, a radio frequency identification ("RFID") chip 26, and an antenna 28 electrically connected or coupled to the RFID chip 26. The RFID chip 26 may include an integrated circuit for controlling RF communication and other functions of the sensor device 20. The antenna 28 is adapted to receive energy from an RF field and produce a signal which is transmitted to one or more external devices, such as a controller or reader or detector, which receives and analyzes the signal.

The RFID chip 26 is also electrically connected to the sensor material 24. The sensor material 24 has an electrical property which varies in the presence of an analyte, such that the signal produced by the antenna 28 will change when an analyte comes into contact with the sensor material 24. If the signal transmitted by the antenna 28 is the same before and after the sensor material 24 is placed in the vicinity of a substance, it is indicative that the substance does not contain any of the target analyte. On the other hand, if the RFID reader detects a difference between the signals, it is indicative that the substance contains an amount of the target analyte.

When the barrier 10 is in the closed condition (FIG. 2), the interior of the sensor device 20 (where the sensor material 24 is positioned) is insulated from the outside environment, rendering it functionally inoperative. When the temperature of the sensor device 20 (or at least the temperature of the barrier 10) changes a sufficient amount, the barrier 10 will move from the closed condition to the open condition (FIGS. 1 and 4) to allow fluid flow through the barrier 10 via the aligned pores 16 and 18. With the barrier 10 in the open condition, fluid from the outside environment may come into contact with the sensor material 24 and the sensor device 20 may be used to signal whether an analyte is present in the fluid. As shown in FIG. 4, at least one of the pore pairs 30 may be configured and oriented so as to be aligned with the sensor material 24 when the barrier 10 is in the open condition. In an alternative embodiment, the first and second pores 16 and 18 are oriented such that all of them will be aligned with the sensor material 24 when the barrier 10 is in the open condition. Aligning the pores with the sensor material 24 ensures that fluid from the outside environment will come into contact with the sensor material 24 when the barrier 10 is in the open condition.

In one embodiment, the sensor device 20 is attached to a product that is normally stored frozen and the barrier 10 is configured to be in the closed condition when the temperature of the surrounding environment is relatively low (e.g., below 0° C.). A typical range in this regard can be between about minus 20° C. and about 0° C. When the temperature of the surrounding environment is sufficiently high (e.g., above 0° C.), the barrier 10 will move to the open condition, thereby exposing the sensor material 24 to fluid present in the outside environment. A typical range in this regard can be between about 0° C. and about 40° C. Different temperatures and temperature ranges for transitioning between the open and closed conditions may also be employed without departing from the scope of the present disclosure.

FIG. 5 illustrates a fluid dispenser device 32 employing the barrier 10 of FIGS. 1 and 2 as an over-laminate that overlays at least a portion of a substrate 34. In particular, the barrier 10 is oriented with the first layer 12 overlaying at least a portion of the substrate 34 and the second layer 14 overlaying at least a portion of the first layer 12. Most preferably, the perimeter of the barrier 10 forms a fluid-tight seal with the substrate 34 to ensure that fluid can only enter the interior of the fluid dispenser device 32 through the pores when the barrier 10 is in the open condition.

The substrate 34 includes a dispensable material 36 that is maintained within the interior of the fluid dispenser device 32 when the barrier 10 is in the closed condition (FIG. 2). When the temperature of the fluid dispenser device 32 (or at least the temperature of the barrier 10) changes a sufficient amount, the barrier 10 will move from the closed condition to the open condition (FIGS. 1 and 5) to allow fluid flow through the barrier 10 via the aligned pores 16 and 18. With the barrier 10 in the open condition, the dispensable material 36 is allowed to flow from the interior of the fluid dispenser device 32 to the outside environment. Preferably, at least one of the pore pairs is configured and oriented so as to be aligned with the dispensable material 36 when the barrier 10 is in the open condition. More preferably, and as shown in the embodiment of FIG. 5, the first and second pores 16 and 18 are oriented such that all of the aligned pairs will be aligned with the dispensable material 36 when the barrier 10 is in the open condition. Aligning the pores with the dispensable material 36 ensures that it will flow into the outside environment when the barrier 10 is in the open condition.

In one embodiment, the fluid dispenser device 32 is incorporated into a patch or dressing for use on a person, such as for wound care objectives, with the dispensable material 36 comprising a treatment fluid (e.g., an antibacterial or skin treatment fluid). The fluid dispenser device 32 is oriented with the second layer 14 positioned against the skin and the barrier 10 in the closed condition. At temperatures sufficiently below human body temperature (e.g., during storage of the fluid dispenser device 32 and shortly after it has first been applied to skin), the barrier 10 remains in the closed condition and the dispensable material 36 remains within the interior of the fluid dispenser device 32. When the temperature of the barrier 10 is sufficiently high (e.g., after it has been positioned against the skin for an adequate amount of time), the barrier 10 will move to the open condition, thereby allowing the dispensable material 36 to flow through the barrier 10 and into contact with the skin. Different temperatures and temperature ranges for transitioning between the open and closed conditions may also be employed without departing from the scope of the present disclosure. For example, the transition temperature may be above human body temperature, such that heat must be applied to the fluid dispenser device 32 following application to the skin for the dispensable material 36 to be released.

In other embodiments, different environmental factors may be employed to move the barrier 10 between the open (FIG. 1) and closed (FIG. 2) conditions. A change in strain may be used to switch between the two conditions, which may be advantageous when incorporated into an RFID label for a product. In an exemplary embodiment, the pores 16 and 18 are aligned when the label is axially stretched and applied to a product. In use, the RFID label may have sensing functions and operate similarly to the sensor device 20 of FIGS. 3 and 4.

In yet another embodiment, the barrier 10 may be moved from the closed condition to the open condition when it has undergone a change in shape, such as that caused by polymerization induced by ultraviolet radiation or another source.

Further, rather than the barrier 10 starting in the closed condition and moving to the open condition upon a suitable change in the environmental factor, the barrier 10 may instead begin in the open condition and then move to the closed condition upon a suitable change or triggering event. Additionally, the barrier may be comprised of more than two layers without departing from the scope of the present disclosure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A device for allowing selective communication between a substrate and an outside environment, comprising:
   a substrate including a sensor material that has an electrical property which varies when an analyte is present, a radio frequency identification (RFID) chip and an antenna, with the chip is electrically connected to the sensor material;
   a first layer overlaying at least a portion of the substrate and having at least one first pore; and
   a second layer overlaying at least a portion of the first layer and having at least one second pore, wherein
   at least a portion of the first and/or second layers are movable with respect to each other between an open condition and a closed condition in response to a change in an environmental factor,
   the first and second pores being substantially aligned in the open condition to allow fluid communication between the substrate and the outside environment such that when the at least one first and second pores are substantially aligned fluid passes through the at the least one first pore and the at least one second pore in the second layer,
   the first and second pores being substantially misaligned in the closed condition to prevent fluid communication between the substrate and the outside environment; and
   wherein the device has a perimeter that forms a fluid tight seal with the substrate.

2. The device of claim 1, wherein the first and second pores are completely misaligned in the closed condition.

3. The device of claim 1, further comprising an RFID chip and antenna associated with the substrate.

4. The device of claim 1, wherein at least one of the first and second layers is comprised of a plastic material.

5. The device of claim 1, wherein at least one of the first and second layers is comprised of aluminum.

6. The device of claim 1, wherein said at least a portion of the first and/or second layers are movable with respect to each other between an open condition and a closed condition in response to a change in temperature.

7. The device of claim 1, wherein said at least a portion of the first and/or second layers are movable with respect to each other between an open condition and a closed condition in response to a change in strain.

8. The device of claim 1, wherein the first and second pores comprise laser-formed pores.

9. A method for exposing a sensor to an environment, comprising:
   providing a sensor separated from an environment by a first layer having a first pore and a second layer having a second pore;
   positioning the first and second pores substantially out of alignment with each other;
   changing an environmental factor, thereby moving the first and second pores into substantial alignment with each other and exposing the sensor to the environment via the first and second pores; and wherein the sensor has a perimeter that forms a fluid tight seal with the substrate.

10. The method of claim 9, wherein said positioning the first and second pores substantially out of alignment with each other includes positioning the first and second pores completely out of alignment with each other.

11. The method of claim 9, wherein said changing an environmental factor includes changing the temperature of the first and/or second layers.

12. The method of claim 9, wherein said changing an environmental factor includes applying a strain to the first and/or second layers.

\* \* \* \* \*